(12) United States Patent  (10) Patent No.: US 8,346,351 B2
Hadley  (45) Date of Patent: Jan. 1, 2013

(54) METHODS FOR QUANTIFYING QT-RR (76) Inventor: David M. Hadley, Woodinville, WA (US)

( * ) Notice: Subject to any disclaimer, the term of this patent is extended or adjusted under 35 U.S.C. 154(b) by 281 days.

(21) Appl. No.: 12/693,351

(22) Filed: Jan. 25, 2010

(65) Prior Publication Data

US 2010/0191133 A1  Jul. 29, 2010

Related U.S. Application Data

(60) Provisional application No. 61/147,429, filed on Jan. 26, 2009, provisional application No. 61/169,259, filed on Apr. 14, 2009.

(51) Int. Cl.
  *A61B 5/04* (2006.01)
(52) U.S. Cl. .................. 600/516; 600/515; 600/517
(58) Field of Classification Search .......... 600/508–509, 600/515–518
  See application file for complete search history.

(56) References Cited

U.S. PATENT DOCUMENTS

| 7,123,953 | B2 | 10/2006 | Starobin et al. | |
|---|---|---|---|---|
| 2001/0020136 | A1 | 9/2001 | Sweeney et al. | |
| 2002/0062088 | A1* | 5/2002 | DePasquale et al. | 600/516 |
| 2003/0130586 | A1 | 7/2003 | Starobin et al. | |
| 2003/0149370 | A1* | 8/2003 | Starobin et al. | 600/515 |
| 2008/0114411 | A1 | 5/2008 | Lian et al. | |

OTHER PUBLICATIONS

Ahnve, S., Correction of the QT Interval for Heart Rate: Review of Different Formulas and the Use of Bazett's Formula in Myorcardial Infarction, American Heart Journal, vol. 1, No. 3, Part 1, pp. 568-574, Mar. 1985.

Aster, R.C. et al., Parameter Estimation and Inverse Problems, Academic Press, 320 pages, Dec. 2004.
Batchvarov, V.N. et al., QT-RR Relationship in Healthy Subjects Exhibits Substantial Intersubject Variability and High Intrasubject Stability, Am J Physiol Heart Circ Physiol, vol. 282, pp. H2356-H2363, Jun. 2002.
Bazett, H.C., An Analysis of the Time-Relations of Electrocardiograms, Heart, vol. VII, No. 4, pp. 353-370, 1920.
Benatar, A. et al., Comparison of Formulae for Heart Rate Correction of QT Interval in Exercise ECGs from Healthy Children, Heart, vol. 86, pp. 199-202, Apr. 2001.
Funck-Brentano, C., Rate-Corrected QT Interval: Techniques and Limitations, The American Journal of Cardiology, vol. 27, pp. 17B-22B, Aug. 1993.
Hodges, M. et al., Bazett's QT Correction Reviewed: Evidence That a Linear QT Correction for Heart Rate is Better, J Am Coll Cardiol, vol. 1, (abstract only), 1983.
Jackson, D.D., Interpretation of Inaccurate, Insufficient and Inconsistent Data, Geophys. J.R. astr. Soc., pp. 97-109, Jun. 1972.

(Continued)

*Primary Examiner* — Rex R Holmes
(74) *Attorney, Agent, or Firm* — Perkins Coie LLP (57) ABSTRACT

Methods and apparatus for determining a patient specific QT-RR curve. One embodiment of a method in accordance with the technology comprises providing electrophysiological data for a specific patient. The method can further include: (a) determining QT durations and RR values for a plurality of heart beats of the specific patient from the electrophysiological data; (b) ascertaining effective RR intervals for the plurality of heart beats by weight-averaging the RR values according to the equation Effective $RR_i = C \times$ Effective $RR_{i-1} + (1-C) \times [RR_{weighted}]$, where C is a number between 0 and 1, and where $RR_{weighted}$ is based on an observed $RR_i$ value and a trend predicted RR value; and (d) finding a value $C_f$ defined by a value of C where a curve fitted to the QT durations and the ascertained effective RR intervals is within a desired standard deviation.

15 Claims, 12 Drawing Sheets

OTHER PUBLICATIONS

Karjalainen, J. et al., Relation Between QT Intervals and Heart Rates From 40 to 120 beats/min in Rest Electrocardiograms of Men and a Simple Method to Adjust QT Interval Values, JACC, vol. 23, No. 7, pp. 1547-1553, Jun. 1994.

Kawataki, M. et al., Relation Between QT Interval and Heart Rate. Applications and Limitations of Bazett's Formula, J. Electrocardiology, vol. 17, No. 4, pp. 371-375, Oct. 1984.

Kovacs, S.J., The Duration of the QT Interval as a Function of Heart Rate: A Derivation Based on Physical Principles and a Comparison to Measured Values, American Heart Journal, vol. 110, No. 4, pp. 872-878, Oct. 1985.

Malik, M. et al., Relation Between QT and RR Intervals is Highly Individual Among Healthy Subjects: Implications for Heart Rate Correction of the QT Interval, Heart, vol. 87, pp. 220-228, Mar. 2002.

Malik, M. et al., Subject-Specific Profiles of QT/RR Hysteresis, Am J Physiol Heart Circ Physiol, vol. 295, No. 6, pp. H2356-H2363, Oct. 2008.

Malik, M., Problems of Heart Rate Correction in Assessment of Drug-Induced QT Interval Prolongation, Journal of Cardiovascular Electrophysiology, vol. 12, No. 4, pp. 411-420, Apr. 2001.

Meyer, J.S. et al., Sudden Arrhythmia Death Syndrome: Importance of the Long QT Syndrome, American Family Physician, vol. 68, vol. 3, pp. 483-488, Aug. 2003.

Pueyo, E. et al., Characterization of QT Interval Adaptation to RR Interval Changes and Its Use as a Risk-Stratifier of Arrhythmic Mortality in Amiodarone-Treated Survivors of Acute Myocardial Infarction, IEEE Transactions on Biomedical Engineering, vol. 51, No. 9, pp. 1511-1520, Sep. 2004.

Pueyo, E. et al., Estimation of the QT/RR Hysteresis Lag, Journal of Electrocardiology, vol. 36, Supp. 1, pp. 187-190, Dec. 2003.

Sagie, A. et al., An Improved Method for Adjusting the QT Interval for Heart Rate (the Framingham Heart Study), American Journal of Cardiology, vol. 70, pp. 797-801, Sep. 1992.

Sohn, R.A., Application of Maximum Likelihood and Bootstrap Methods to Nonlinear Curve-Fit Problems in Geochemistry, Geochemistry Geophysics Geosystems, vol. 3, No. 7, pp. 1-17, Jul. 2002.

Taran, L.M. et al., The Duration of the Electrical Systole (Q-T) in Acute Rheumatic Carditis in Children, American Heart Journal, vol. 33, pp. 14-26, Jan. 1947.

Search Report and Written Opinion issued Mar. 23, 2010 in International Application No. PCT/US2010/022007.

* cited by examiner

METHODS FOR QUANTIFYING QT-RR

CROSS-REFERENCE TO RELATED APPLICATIONS

This application claims priority to U.S. Provisional Patent Application No. 61/147,429 filed Jan. 26, 2009 and U.S. Provisional Patent Application No. 61/169,259 filed Apr. 14, 2009, both of which are incorporated herein by reference.

TECHNICAL FIELD

The present invention relates to methods and apparatus for determining a subject specific QT versus RR curve derived from physiologic signal representative of a subject's heart activity.

BACKGROUND

Individuals with an abnormally long QT interval (long QT syndrome, LQTS) have a higher risk of spontaneous fatal arrhythmias [1]. Numerous studies have quantified QT versus RR behavior in various populations to improve methods for risk stratification [2-12]. The accumulative effect of these studies has been to highlight the tremendous variability in the QT-RR relationship and the large associated uncertainty. More recent studies [13, 14] have shown that the QT-RR relationship is patient specific and general trends derived from population studies may lead to faulty interpretations when applied to observations from a single subject.

Figure 1:
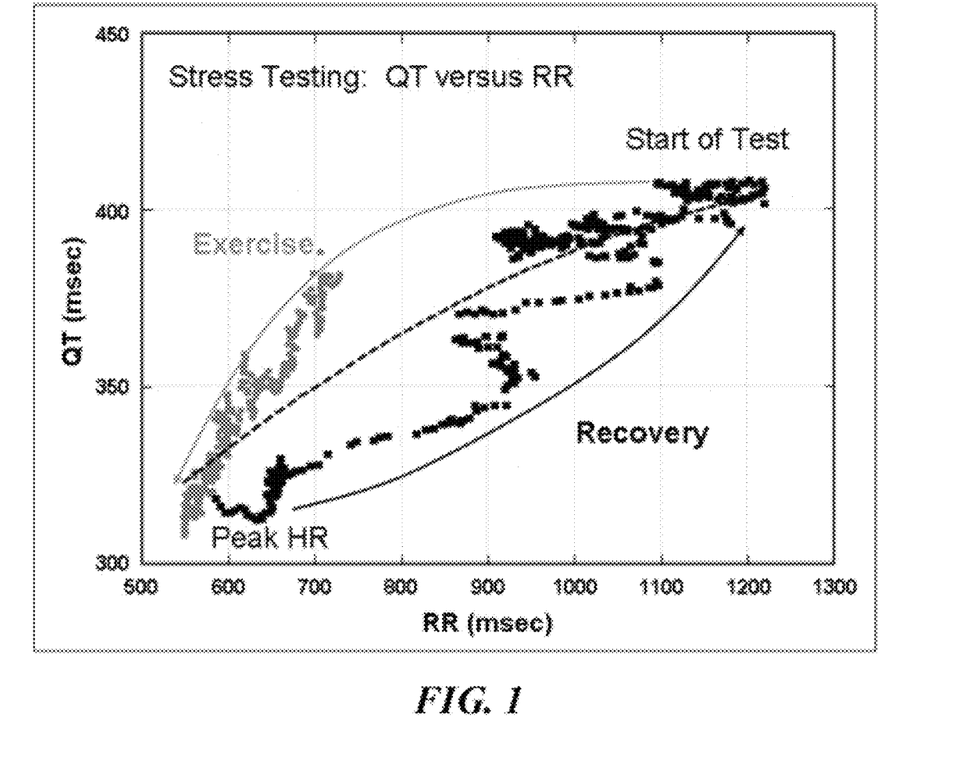
FIG. 1 is a graph of QT-RR dispersion and hysteresis observed over the course of a routine cardiac stress test.

The measurement of the QT-RR relationship is further complicated by the heart's "memory" of the preceding beat history, resulting in a hysteresis with multiple values of QT associated with single values of RR, depending upon the longer term increasing or decreasing trend of heart rate. Traditional QT-RR curves are based upon the assumption that each QT-RR point on the curve reflects the QT value that would be observed if the heart beat at a constant rate for a sufficiently long period such that all memory of previous beats with different RR intervals was forgotten—a condition that could only exist if the subject's heart was electrically paced. This issue is highlighted in FIG. 1 which shows a more typical clinical example of QT-RR recorded during a cardiac stress test where the patient exhibits five distinct values of QT for RR~920 msec with a 50 msec range in observed QT values. Previous investigators have attempted to use the observed hysteresis, or difference in QT between the exercise and recovery phases, as a metric for cardiac arrhythmia risk stratification [Starobin, et al. U.S. Pat. No. 7,123,953]. More recent studies [15, 16, 17] have modeled the effective cycle length associated with each QT observation, derived from 24-hour ambulatory ECG (Holter) records, as a sum of weighted RR intervals for the preceding ~150 beats. The method solves a system of equations where each preceding RR interval weight is an unknown—essentially a system of equations with ~150 unknowns. This complex methodology is successful in modeling some aspects of patient-specific QT-RR hysteresis.

Many drugs have been found to prolong QT, thus increasing patient risk and driving extensive clinical testing of new therapeutic agents affects on QT duration as part of the Food and Drug Administration (FDA) approval and labeling process. Unexpected prolongation of the QT interval is the major cause of drug withdrawal from the market and for delays in FDA approval. These studies are mainly done using short recordings of patients' resting ECGs taken pre and post administration of the target drug. Because of normal heart rate variability and other factors that may alter the patient's resting rate, the recorded QT values are associated with a range of RR values. To make the assessment of the drug's impact on QT, the recorded values must be corrected to a constant value of RR, know as QTc (corrected QT). The QTc formulas used to correct the raw QT-RR values have been the subject of numerous studies and the community has serious concerns about the validity of the corrections. Further, the scatter in QTc is substantial and the cohort size required to power a statistically meaningful assessment results in very high clinical drug testing costs.

Although the clinical understanding of the observed dispersion and hysteresis of QT-RR is high, there is no simple methodology to develop patient specific QT-RR curves in support of the assessment of patient's risk for LQTS and cardiovascular death or for rapid and cost effective assessment of therapeutic agents.

SUMMARY

Several embodiments of the technology are broadly directed to the assessment and determination of the patient specific QT versus RR relationship, including an assessment of uncertainty and confidence limits. Methods for the determination of this relationship may lead to improved risk stratification associated with prolonged or abnormal QT behavior and improved drug testing accuracy and cost effectiveness for meeting FDA mandated clinical QT studies.

Figure 2:
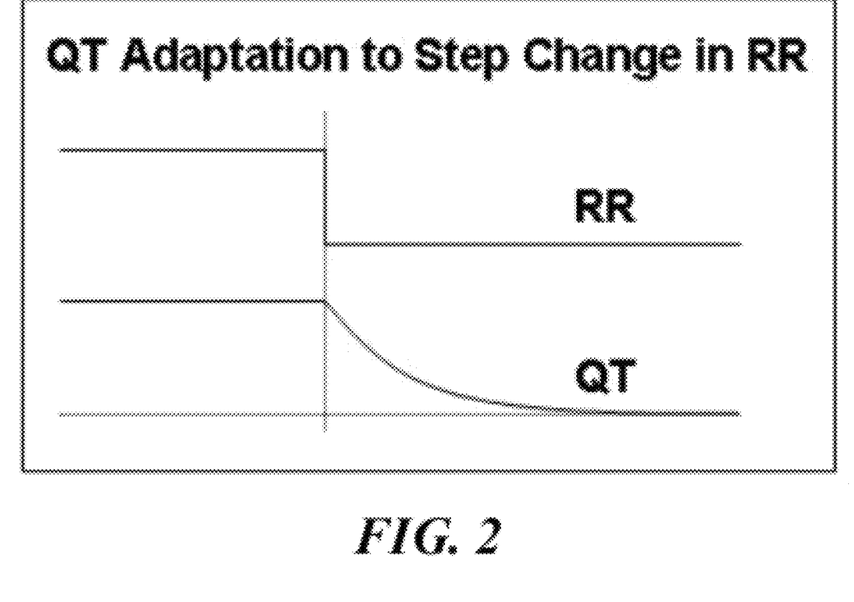
FIG. 2 is a graph illustrating behavior of QT associated with an abrupt change in electrical pacing of the heart.

One feature of several embodiments of this technology is the development of an "Effective Heart Rate" or "Effective RR Interval". FIG. 2 illustrates this concept with a common example from clinical pacing experiments. Initially the patient is paced at a constant heart rate (HR), corresponding to a constant RR interval (=60/HR). The pacing protocol is abruptly increased to a higher HR (smaller RR), but the observed QT does not instantaneously adjust to the shortened RR interval, resulting in a wide range of QT values for a single RR value. Cardiac mechanisms that result in changes in the duration of the QT phase of the cardiac cycle slowly adapt to the new rate. The observed QT reflects an effective RR rate that is influenced by both the most recent RR interval as well as the previous beat rate history. We define the effective RR rate as the constant pacing rate that would be associated with the observed QT value. Selected embodiments of the technology can also include the determination of a patient specific model that relates the effective RR interval at each beat to the preceding beat history.

A further embodiment of the technology includes the combination of the determined effective RR interval history with the observed QT values to determine a unique patient specific QT-RR curve. The technology can further include a methodology to assess the statistical confidence limits at selected points along the determined QT-RR curve. The technology may be used with QT-RR values determined by measurement methods well known to practitioners of the art using ECG recordings from Holter monitoring, cardiac stress testing, bedside monitors and other ECG recording mechanisms.

Several embodiments of the technology also include the use of the derived QT-RR curve and the associated confidence limits in the assessment of patient risk for LQTS. Multiple determinations of the QT-RR curve and associated confidence limits may also be used to quantify the pre and post effects of therapeutic agents on QT duration for numerous values of HR.

DETAILED DESCRIPTION

The following discussion is presented to enable a person skilled in the art to practice the invention. Various modifications to the disclosed embodiments will be apparent to those skilled in the art, and the generic principles herein may be applied to other embodiments and applications without departing from the spirit and scope of the present invention as defined by the appended claims. Thus, the present invention is not intended to be limited to the embodiments presented, but is to be accorded the widest scope consistent with the principles and features disclosed herein.

Figure 3:
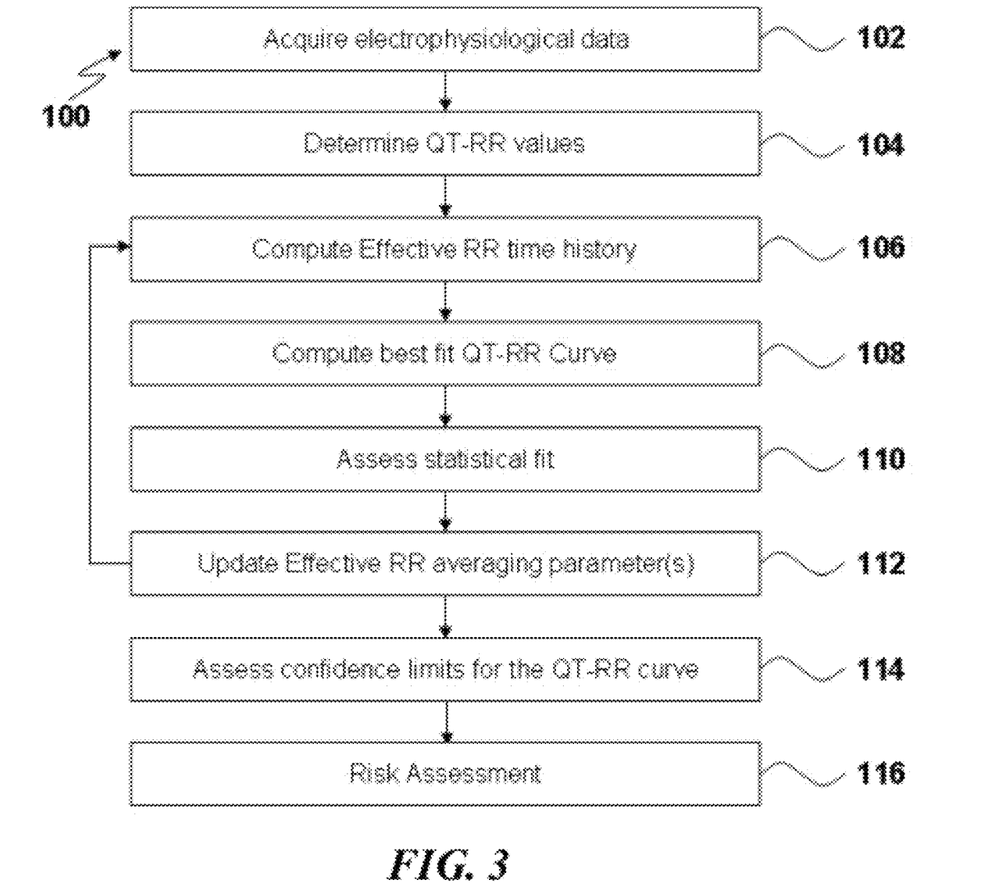
FIG. 3 is a flowchart of a method for determining a patient specific QT-RR curve in accordance with an embodiment of the technology.

FIG. 3 is a flow chart of method 100 for determining the patient specific QT-RR curve and the associated confidence limits. Method 100 includes a first stage 102 comprising acquisition of the electrophysiological data (e.g.: ECG time series) of sufficient time duration and over a range of increasing and decreasing heart rates. Method 100 also includes stage 104 comprised of measuring the duration of the QT intervals and the associated beat-to-beat RR intervals.

Method 100 continues to stages 106 through 112 wherein iterative stages find the optimal QT-RR curve and associated effective RR averaging parameter(s). Stage 106 computes the effective RR time series for a starting value of the averaging parameters. Stage 108 computes the optimal QT-RR curve for the corrected RR values and Stage 110 assesses the statistical properties of the scatter between the derived QT-RR curve and the observations. Stage 112 updates the estimate for the Effective RR averaging parameters and either continues with stage 106 for another iteration or determines that a satisfactory model has been found and progresses to stage 114. This next stage assesses the statistical reliability of the derived QT-RR curve. The final stage 116 of Method 100 combines the derived QT-RR curve with industry standard ranges of expected normal values and with previously derived curves and their associated confidence limits for the comparison of QT behavior for assessing the risk of LQTS and for assessing the impact of therapeutic agents on QT duration. Although FIG. 3 illustrates an embodiment of the method 100 that includes stages 102-116, other embodiments may include only a subset of stages 102-116 or additional stages. For example, another embodiment of the method 100 can include stages 102, 104, 106 and 108.

A. Data Source and QT-RR Measurements.

The first stage of 102 of the embodiment of this method 100 involves acquisition of electrophysiological data from a data source using a suitable protocol. For some patients the effective cardiac memory of the beat history can extend for approximately 100-200 beats and reliable estimates of the heart's current state can not be made until the heart has forgotten the unknown previous RR history (e.g., the previous RR history no longer influences the present heart function). For this reason it is helpful to initially record about five minutes of resting ECG data before the start of the exercise phase of the protocol. Next the patient exercises over a period of about 10 minutes with a protocol designed to bring the patient's heart rate to a higher or maximum value at the end of the period. Finally the patient should be placed in a comfortable resting position and the heart rate allowed to return to normal over a final recording period of 10-15 minutes. Clinical standard twelve-lead ECG stress testing systems are well suited to this protocol. However, those experienced in the art will recognize that the ECG data could be recorded using Holter or other ECG monitoring systems and the ECG data selected from a segment of the record wherein the patient's heart rate cycles through a suitably large RR range. Several embodiments of the method are insensitive to the direction of the HR cycle—either increasing or decreasing in the initial phase.

Figure 4:
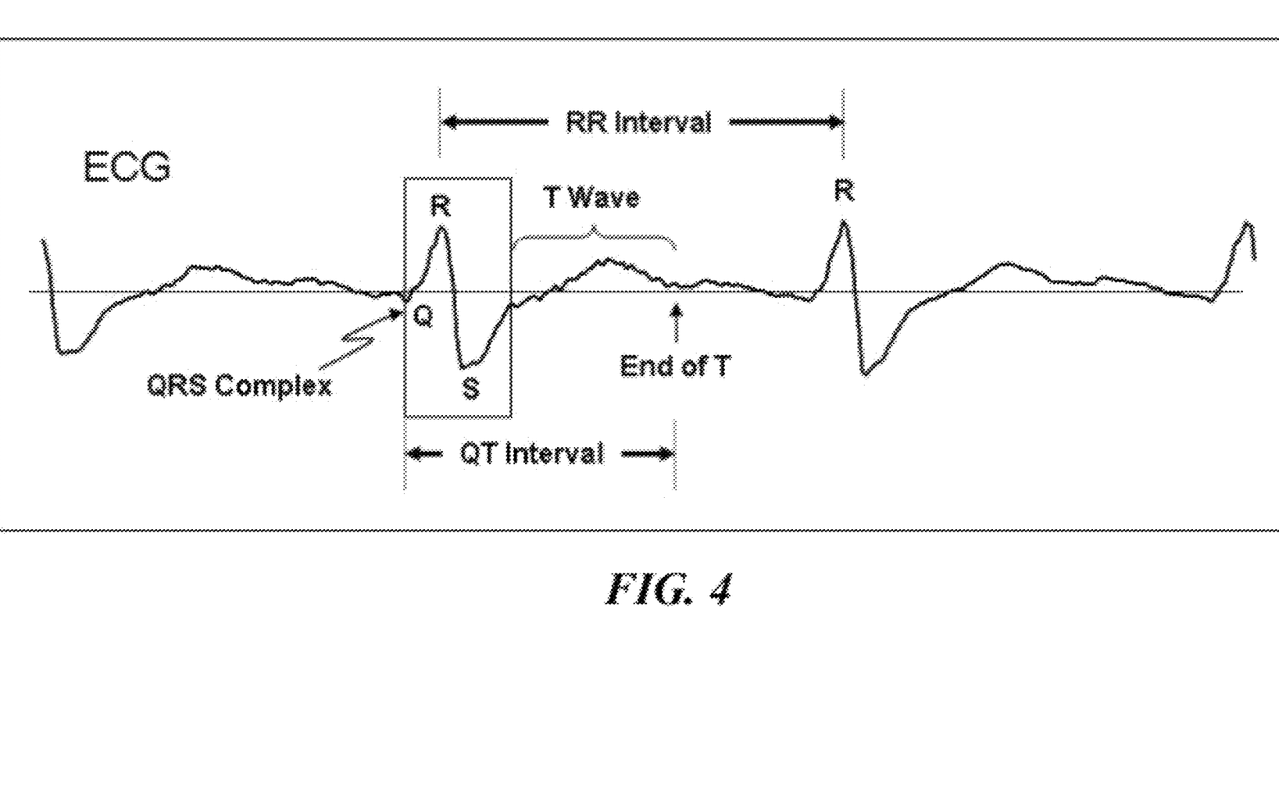
FIG. 4 is an ECG trace highlighting QT and RR measurements.
Figure 5:
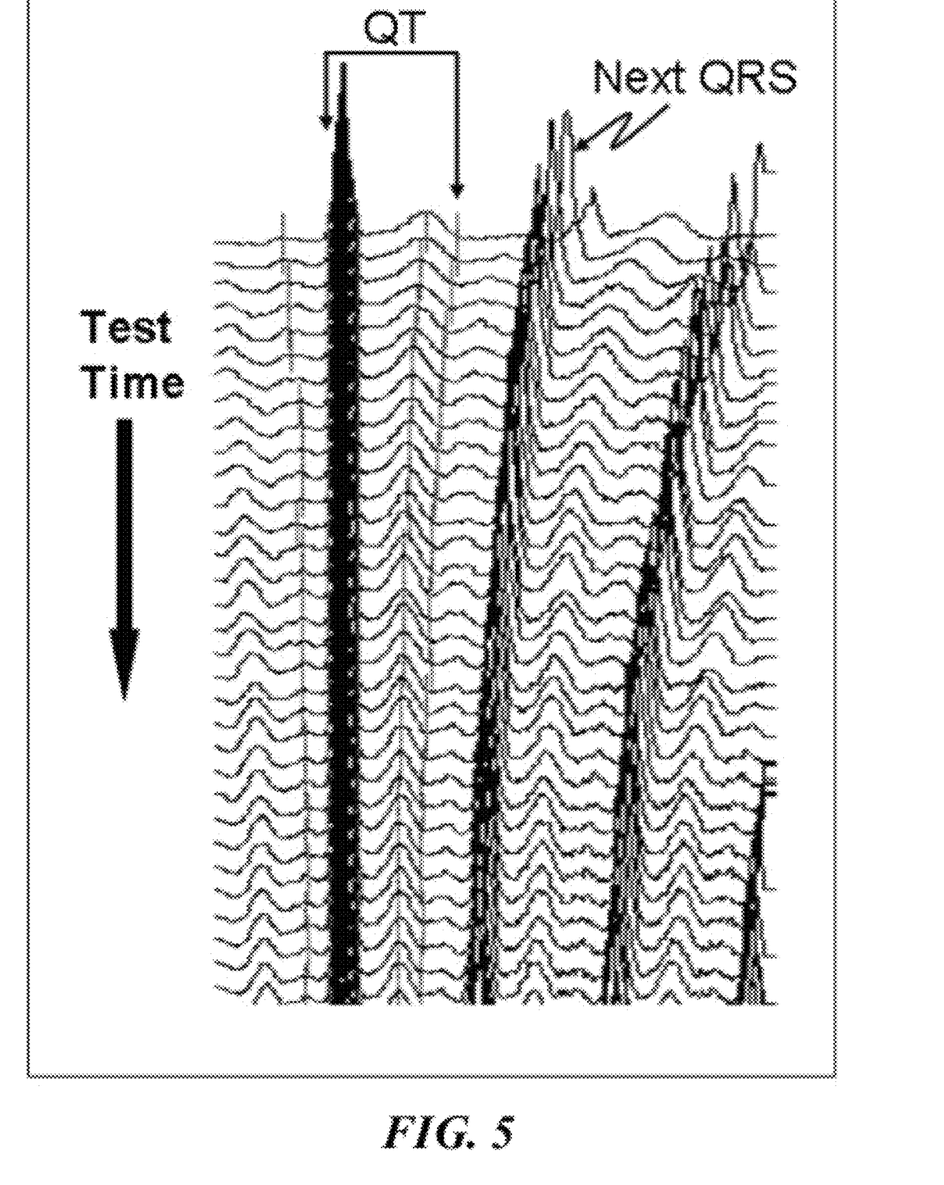
FIG. 5 is a chart of a series of ECG tracings over the course of a stress test showing QT behavior as heart rate increases.

Following the acquisition of the ECG data the method progresses to stage 104 wherein the QT and RR measurements are obtained. FIG. 4 illustrates a single ECG trace with key phases indicated. The QRS complex reflects the electrical signal associated with the depolarization of the ventricles. The following broad "bump" is the T-Wave and records the electrical signature of the repolarization of the ventricles as the cardiac cycle ends and heart returns to a resting state before the next beat cycle. The QT interval is the time duration from the onset of the QRS cycle (start of Q) to the end of the T-Wave. The time between a beat and the previous beat is commonly measured between peak R waves and is know as the RR interval for the beat; the associated heart rate is 60/RR (in seconds). FIG. 5 shows a series of ECG tracings over the course of a segment of a stress test illustrating the effects of increasing heart rate. The figure has been plotted with the QRS complex aligned for each increasing time step. As heart rate increases with exercise during the test (note the decreasing RR interval to the next QRS complex), the associated QT interval shortens. FIG. 5 illustrates the dynamic association between QT and RR. Part of the input to stage 106, discussed below, is the RR time series measured for every beat for the entire protocol.

As those experienced with the art of QT measurement will recognize, there are many well known algorithms for determining the duration of QT and a description of these methods is outside of the scope of method 100. We have found that methods that stack several beats together to improve signal to noise are helpful, particularly during exercise phases of the protocol. The resulting QT duration is associated with the time of the middle beat in the stack. However, for low noise ECG recordings or other applications, the method for determining QT can be applied on a beat by beat basis. Estimates of QT and RR uncertainty associated with any ambiguity in defining the QT interval or with the range of RR times for the selected beats in the stack is useful additional information that may be used in weighting the importance of each QT-RR measurement in stage 108 discussed below.

B. Determining the Effective RR Time Series and QT-RR Curve

Stage 106 of Method 100 computes the effective RR time series. In the simple cardiac pacing example discussed above and presented in FIG. 2, the QT interval adapts with each beat to the higher heart rate. This observation motivates the concept of an effective RR interval; the observed QT interval is associated with an effective RR interval that reflects the previous history of RR intervals within the span of cardiac beat memory for the individual subject. A simple model that captures this concept is that the effective RR interval for the most recent beat is a weighted average between the effective RR interval from the preceding beat and the most recent RR interval. Computationally, with each new beat (i) the effective RR value is updated as a weighted average of the last computed effective RR value, associated with the previous (i-1) beat, and the RR value associated with the most recent beat:

$$\text{Effective}RR_i = C \times \text{Effective}RR_{i-1} + (1-C) \times [RR_i]$$
$$[0 \leq C \leq 1] \quad (1)$$

Figure 6:
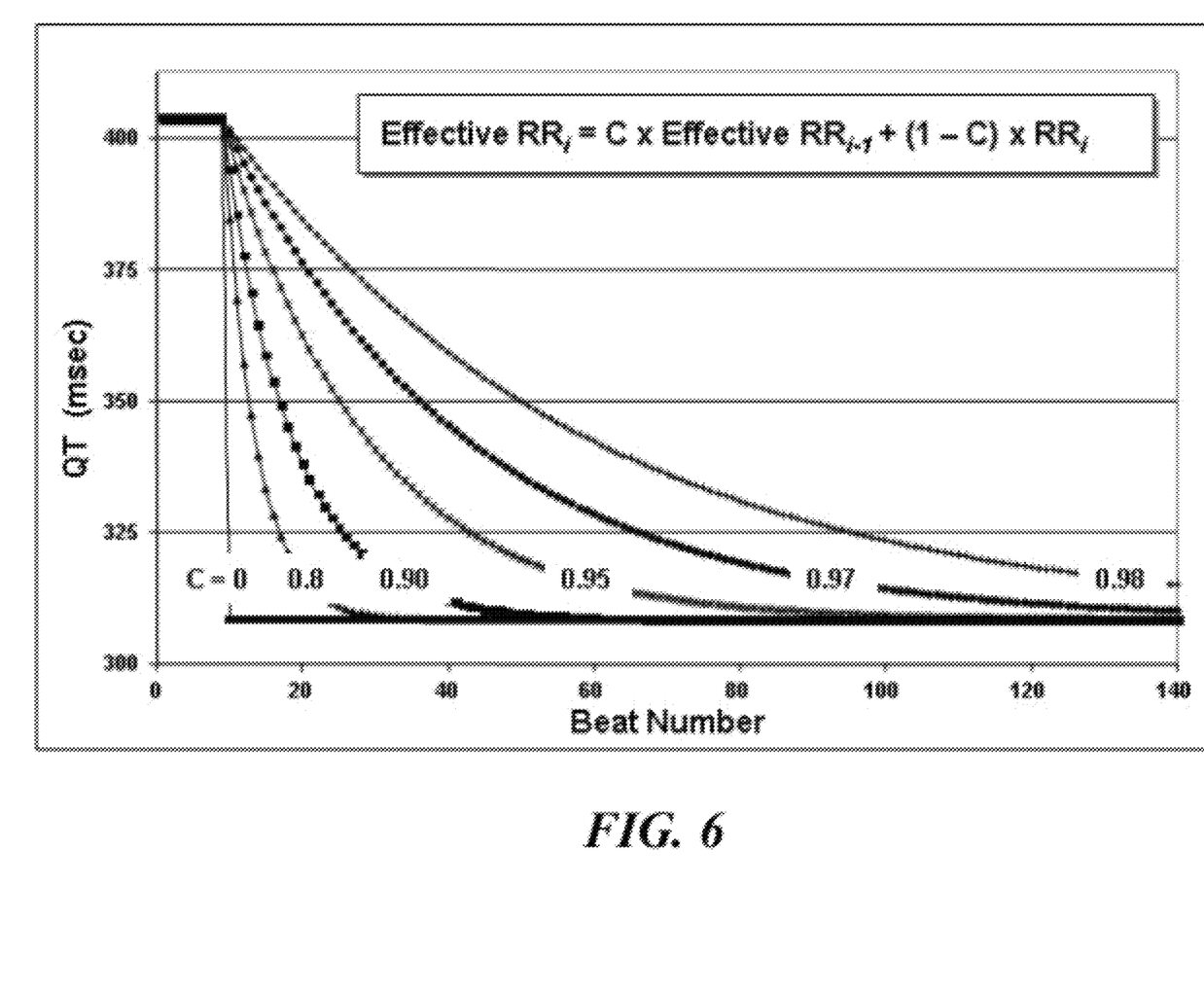
FIG. 6 is a graph of effective RR interval for an abrupt change in electrical pacing for various values of the parameter C.

The parameter C controls how fast the effective RR value adapts to changes in heart rate. FIG. 6 shows an example with a step increase in heart rate from 70 to 90 beats per minute (RR decrease from 857 msec to 667 msec). For C=0 the effective RR value updates with each new beat to the most recent RR value—there is no weighted averaging. As C increases the associated effective RR curve adapts to the rate change over progressively longer time intervals. For the extreme case of C=1, the effective RR value would never adapt to changes in heart rate. Those experienced in the art will recognize that the adaptation rate could be modeled in more complex relationships, involving functional relationships for C that are dependent upon $RR_i$.

Recursively substituting $\text{Effective}RR_n$, for n preceding RR intervals (n=0 is the most recent RR interval, n=1 is the preceding RR, etc.), leads to the following relationship:

$$\text{Effective}RR_i = \sum_n C^n \times [(1-C) \times RR_{i-n}] \quad (2)$$

where n is sufficiently large that $C^n$ approaches zero and the effects of beats older than n have negligible influence on the current effective RR value, i.e. the heart has forgotten the influence of beats older than n. As the heart beats each new RR value contributes to the effective RR value by the weighted average term:

$$[(1-C) \times RR_i] \quad (3)$$

The influence of each beat diminishes as beats progress, following the series $C^1, C^2, C^3, \ldots C^n$. It is useful to define a beat half-life as being the number of beats, HL, that must occur before the influence of a particular beat has fallen by 50 percent, i.e.:

$$C^{HL} = 0.50 \text{ or } HL = \frac{\text{Log}(0.50)}{\text{Log}(C)} \quad (4)$$

As an example, C=0.98 implies a half life of 34 beats, i.e., after 34 beats the initial influence of an RR interval has fallen by 50 percent of its initial value.

Given a continuous RR interval time series and a trial value of C, recursive application of Equation (1) results in an associated effective RR interval time series. Computationally, the initial value for the first effective RR interval is set to the first RR interval and the effective RR interval time series is not considered valid until several half-lives for the associated C have passed, i.e.: memory of the preceding unknown beat history has faded. Finally, the QT-RR measurements from stage 104 are updated with the effective RR interval associated with each measurement, i.e., each observed RR, is replaced by each associated $\text{Effective}RR_i$. For QT-RR values derived from a suite of signal averaged beats, the RR value associated with the middle beat in the stack is chosen as the associated $RR_i$.

Figure 7A:
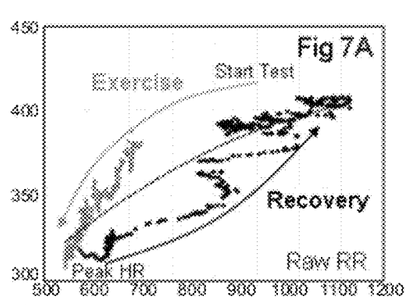
FIGS. 7A-7F are graphs plotting QT-RR hysteresis examples for different values of beat half life and the reduction in associated dispersion.
Figure 7B:
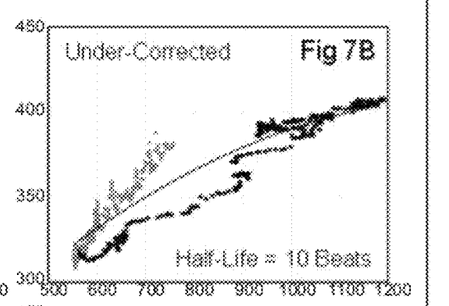
Figure 7C:
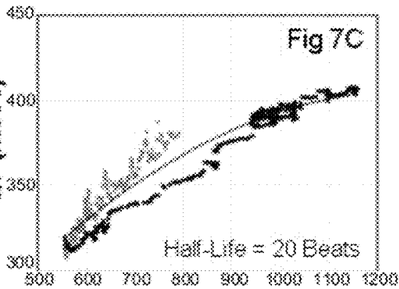
Figure 7D:
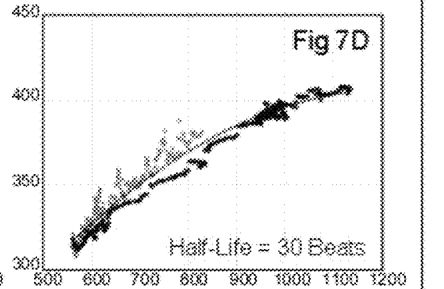
Figure 7E:
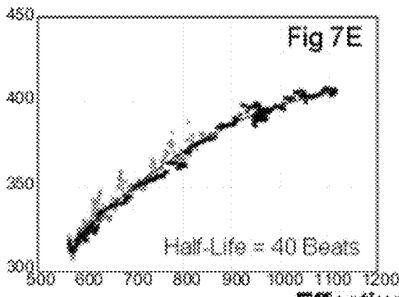
Figure 7F:
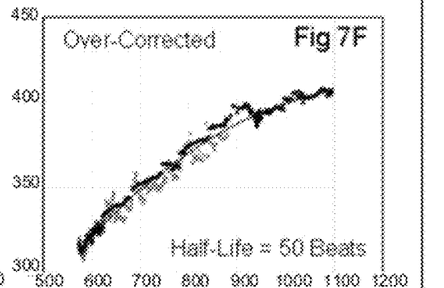

FIGS. 7A-7F are plots for an exercise test for various values of C. FIG. 7A is the raw uncorrected QT-RR data, showing substantial hysteresis and large scatter. The gray circles are the QT-RR values obtained during the Exercise phase of the protocol and the black squares are from the Recovery phase. As C and the associated half-life increase, the hysteresis and scatter collapse (FIGS. 7B-7D) until the exercise derived QT values co-mingle with the recovery values as shown in FIG. 7E. In FIG. 7F the effective RR intervals have been overcorrected and the exercise and recovery data have passed through each other.

Figure 8A:
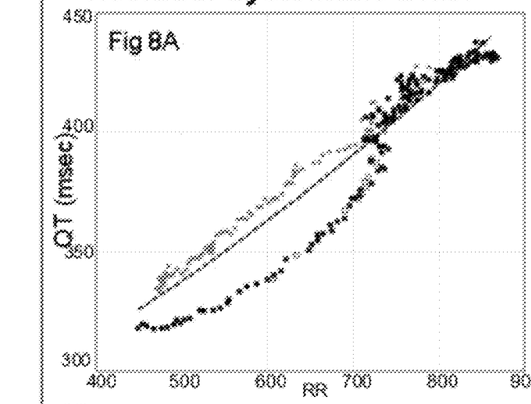
FIGS. 8A-8C are graphs of a QT-RR example illustrating systematic correction bias related to the RR trend of previous beats.
Figure 8B:
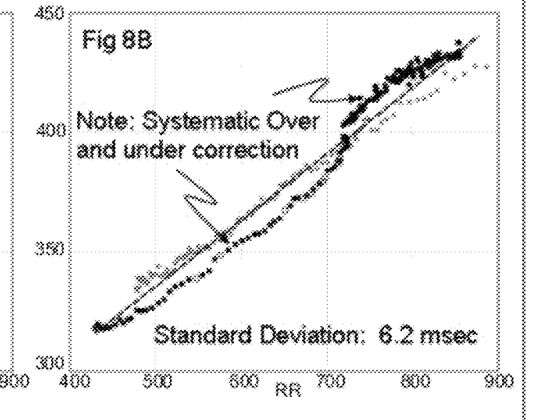
Figure 8C:
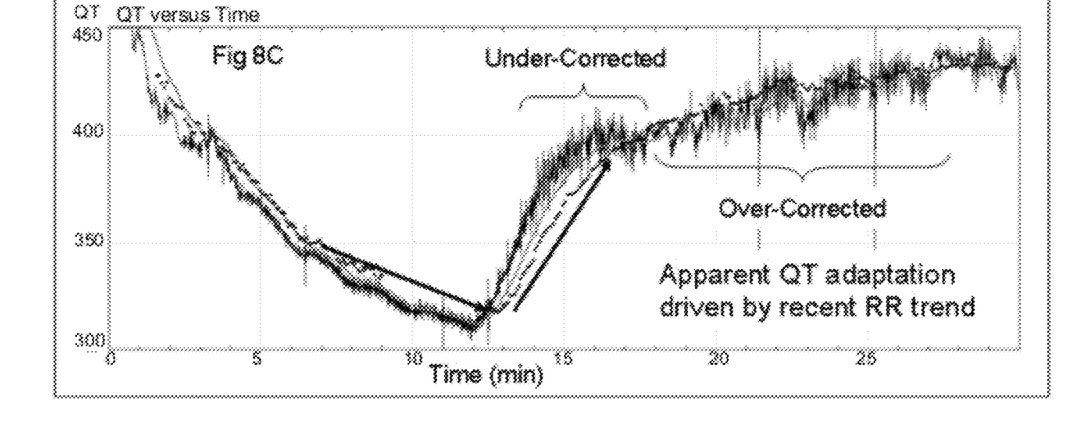

In another embodiment, the effective RR method described in Equation (1) above can be modified to model robustly more complex cardiac behaviors. FIG. 8A illustrates the observed or raw QT-RR hysteresis associated with a patient test and FIG. 8B shows the reduction of the hysteresis scatter using the above recursive application of Equation (1) and finding the optimal value of C. Although the dispersion has been reduced, this analysis shows a clear systematic bias in the reduction of the QT-RR curve. For example, such systematic bias is exhibited by effective RR under-correction at short RR intervals (from ~13 to 16 minutes from the start of the test, FIG. 8C) and over correction at longer intervals (from ~17 to 25 minutes). FIG. 8C shows, over the time history of the stress test, (1) the raw observed RR intervals (black "spiky" curve—converted to QT using the best-fit QT-RR curve in FIG. 8B), (2) the computed best-fit effective RR intervals (gray curve—also converted to QT), and (3) the observed QT values (black squares). The transition from under-corrected to over-corrected occurs when the trend of the effective RR interval curve (gray) abruptly changes slope.

Figure 9:
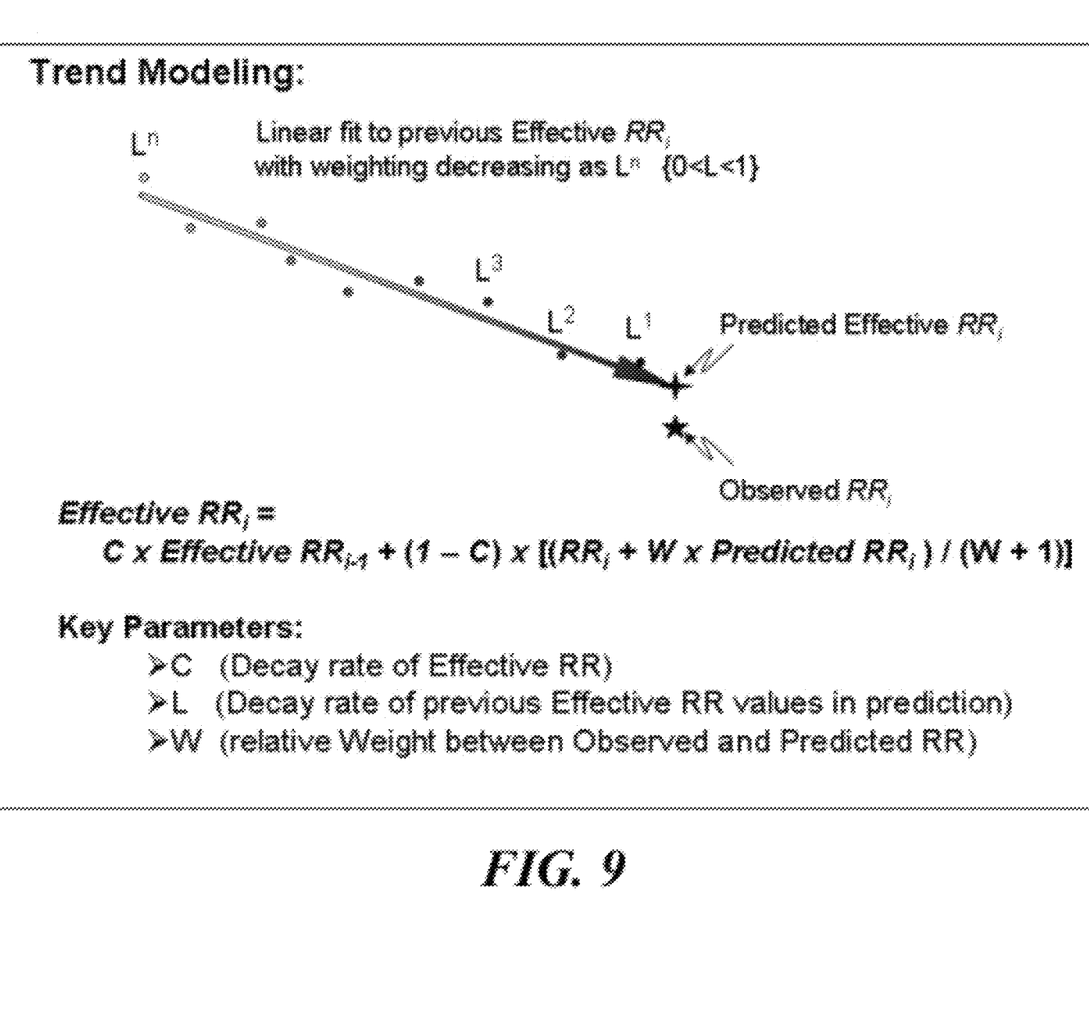
FIG. 9 is a chart of an effective RR Trend Model illustrating the modeling of trends.

This systematic QT behavior over the course of the treadmill test suggests that the heart adapts to a heart-rate trend and adapts QT in anticipation of a continuation of the trend. To accommodate this observation a trending term is added to Equation 1. FIG. 9 illustrates this concept. Preceding effective RR values are fit to a trend line, with the contribution or weight of each value decreasing with RR age as $L^n$, with $0<L<1$ and n is the associated RR interval number before the current interval (i.e.: 1, 2, 3 . . . ). The derived weighted trend line is next used to compute the predicted effective RR value for the current interval and a weighted average between the observed RR interval and the expected trend line interval is computed:

$$(RR_i + W \times \text{Predicted } RR_i)/(1+W) \text{ where } W \geq 0. \quad (5)$$

This term is used to replace the term $[RR_i]$ in Equation (1), forming:

$$\text{Effective } RR_i = C \times \text{Effective } RR_{i-1} + (1-C) \times [(RR_i + W \times \text{Predicted } RR_i)/(1+W)] \quad (6)$$

The primary model parameters are as follows:
C (Decay rate of Effective RR, $0 \leq C \leq 1$)
L (Decay rate of previous Effective RR values in trend prediction, $0<L<1$)
W (relative averaging Weight between Observed and Predicted RR values, $W \geq 0$, Note: W=0 reverts to Equation (1))

Figure 10A:
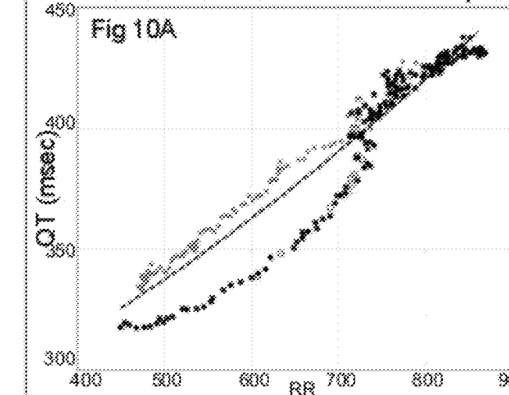
FIGS. 10A-10C are graphs showing QT-RR data of FIG. 8 corrected through inclusion of RR trending information showing a significant reduction in corrected QT scatter relative to FIG. 8.
Figure 10B:
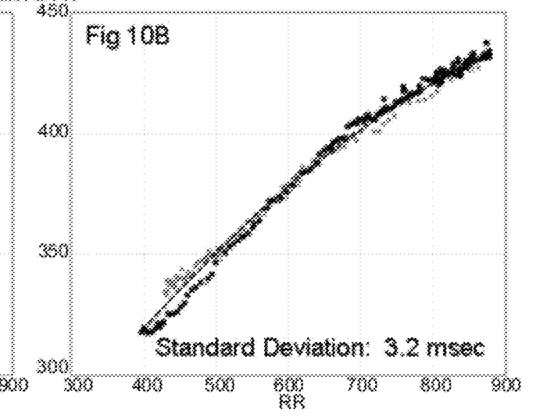
Figure 10C:
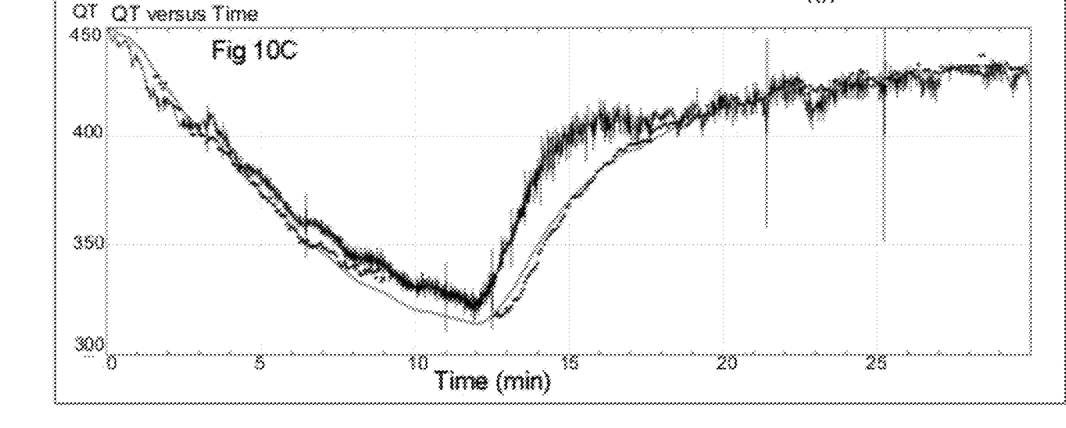

FIGS. 10A-10C illustrate the same data displayed in FIGS. 8A-8C, respectively, but now analyzed by optimizing the primary parameters from Equation (6). Note that the QT-RR dispersion has been significantly reduced and systematic bias has been largely eliminated. Those familiar with modeling physical processes will recognize that the model improvements associated with the addition of the trending term suggests that additional higher order terms, involving for instance the change in trending, may add further benefit in improving the model. Equation (6) illustrates the concept of extending the model, but does not limit the claims to just the two terms involving the raw observation of RR and trend information. Addition of higher order terms is anticipated to further improve the model.

Figure 11:
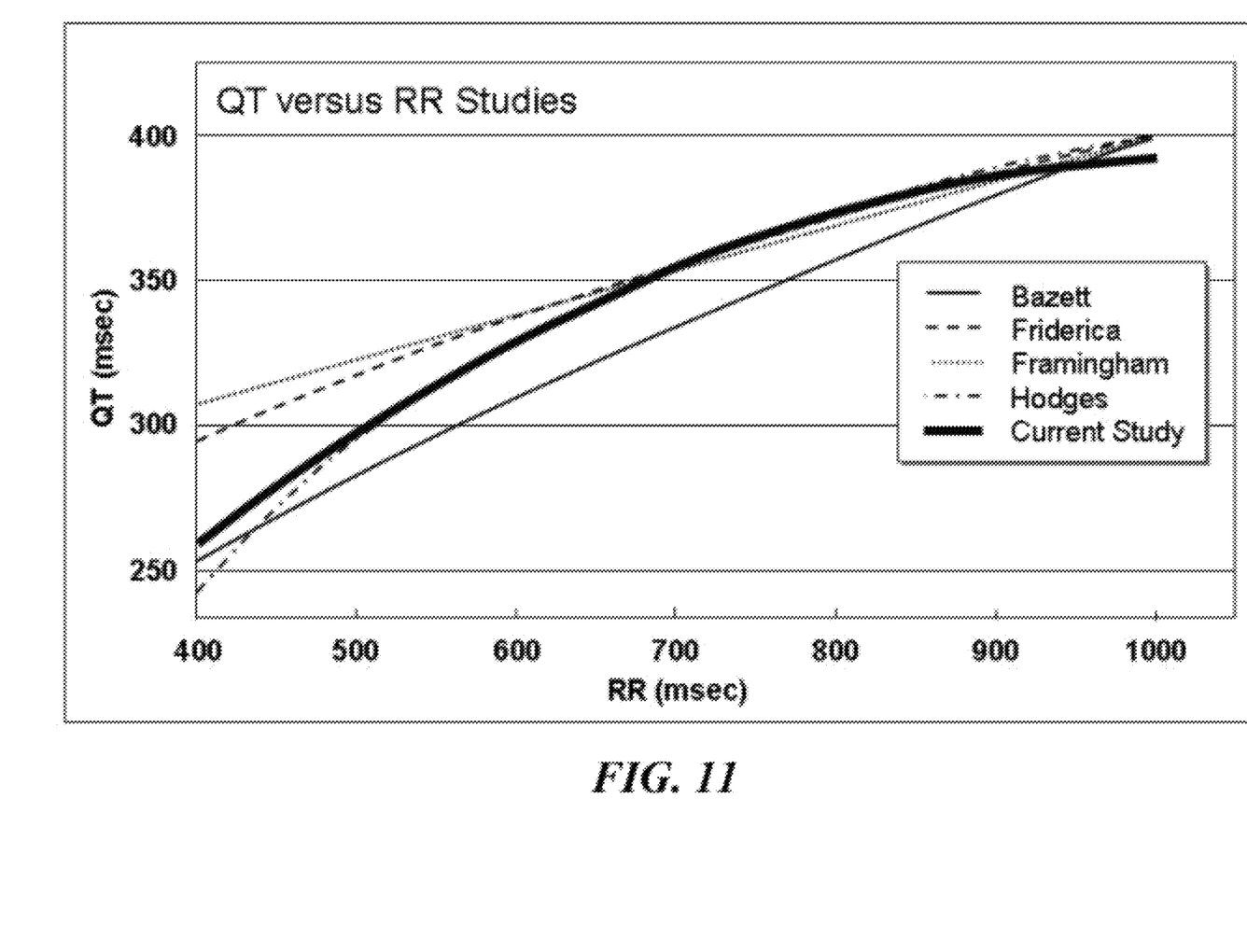
FIG. 11 is a graph illustrating standard reference QT-RR correction curves.

Method 100 continues to stage 108 where a curve is fit to the derived QT-effective RR data from stage 106. Many different functional forms have been studied by previous investigators. FIG. 11 illustrates the functional forms of the curves that are most commonly referenced [2, 3, 5 and 9]. The curves have been anchored to QT=400 msec at RR=1000 msec. As those skilled in the art will recognize, there are many different forms of a curve that could be selected for fitting the data, provided the curve exhibits enough flexibility to model the actual range of observed QT-RR distributions. The inventor's studies of stress test derived QT data, from ~2000 patients and reflecting about 1.5 million individual QT-RR measurements, suggests that a second order polynomial adequately models the data (average standard deviation ~4.4 msec). The derived average curve for the study population is shown in FIG. 11 (bold black line marked as "Current Study"). The selected QT-RR equation is:

$$QT_i = a \times \text{EffectiveRR}_i^2 + b \times \text{EffectiveRR}_i + c \quad (7)$$

The values of a, b, and c can be computed by minimizing the root mean square error between the model curve and the data:

$$\sum_n w_i \times (QT_i - (a \times \text{EffectiveRR}_i^2 + b \times \text{EffectiveRR}_i + c))^2 \quad (8)$$

where $w_i$ are weights associated with the estimated uncertainty of the QT or RR measurements derived in stage 104. The weights may also be adjusted such that unequal sampling between exercise and recovery is normalized or weighted such that the two phases have equal influenced. Simple least squares methods to solving (8) are well known and not reproduced here. Damped and iterative matrix inverse methods may also be used [18, 19] and potentially useful constraints imposed. For instance, it is well known that QT asymptotically approaches a constant value at long RR values and it may be useful to impose a constraint that the derived curve is concave downwards (i.e.: a<0). Alternatively, higher order curves, such as a cubic polynomial, may be used to model the data and, if desired, additional constraints may be imposed that provide asymptotic limits.

Once the values of a, b, and c are determined, then Method 100 continues to stage 110 where Equation (8) is used to compute the standard deviation between the model and the corrected QT-RR data. The statistical measure of goodness of fit drives the iterative search for the optimal value of the primary parameters C, L and W, stage 112. Different strategies can be employed to find the best fit model. A steepest decent method based upon the computed changes in the standard deviation (Equation (8)) with respect to changes in C, L and W can be used to guide the selection of the next estimated key values, continuing to stage 106 until the minimum standard deviation value has been found. Alternatively, as the CPU resources required to execute stages 106-110 are fairly minimal, a course search across a range of primary parameter values can be done quickly, followed by a fine search around the minimum values found in the course search.

Stage 114 of Method 100 assesses the confidence limits for the derived QT-RR curve using a bootstrap method with 100 percent replacement [20]. The QT-RR values from stage 104 are randomly selected until the observed number of QT-RR values have been chosen. A single QT-RR pair may not be selected, or selected one or more times. Stages 106 through 112 are next executed to determine the optimal values of a, b, and c for the selected QT-RR pairs and values of QT are computed at selected RR values (e.g.: RR values corresponding to heart rates of 60, 75, 90, etc), using Equation (7), and saved. This process iterates a few hundred times. For each selected value of RR the saved QT values are sorted largest to smallest and the distribution used to estimate confidence limits. For example, if 200 iterations were performed, then the $5^{th}$ and the $195^{th}$ values of the sorted QT values reflect the 95 percent confidence limit range for the associated RR value. Using Method 100 with QT-RR data obtained from routine stress testing, such as shown on FIG. 7 or 10, it is common to find 95 percent confidence limits in the ±1 msec range.

The final stage 116 of Method 100 compares the resulting QT-RR curve and associated confidence limits, derived in stage 114, with established values to assess risk. For the case of assessment of LQTS the results of stage 114 are compared with QT-RR values derived from studies of patients with LQTS. For assessment of the therapeutic affects on QT, the QT-RR curves from assessments made pre and post administration of the target drug are compared.

Figure 12:
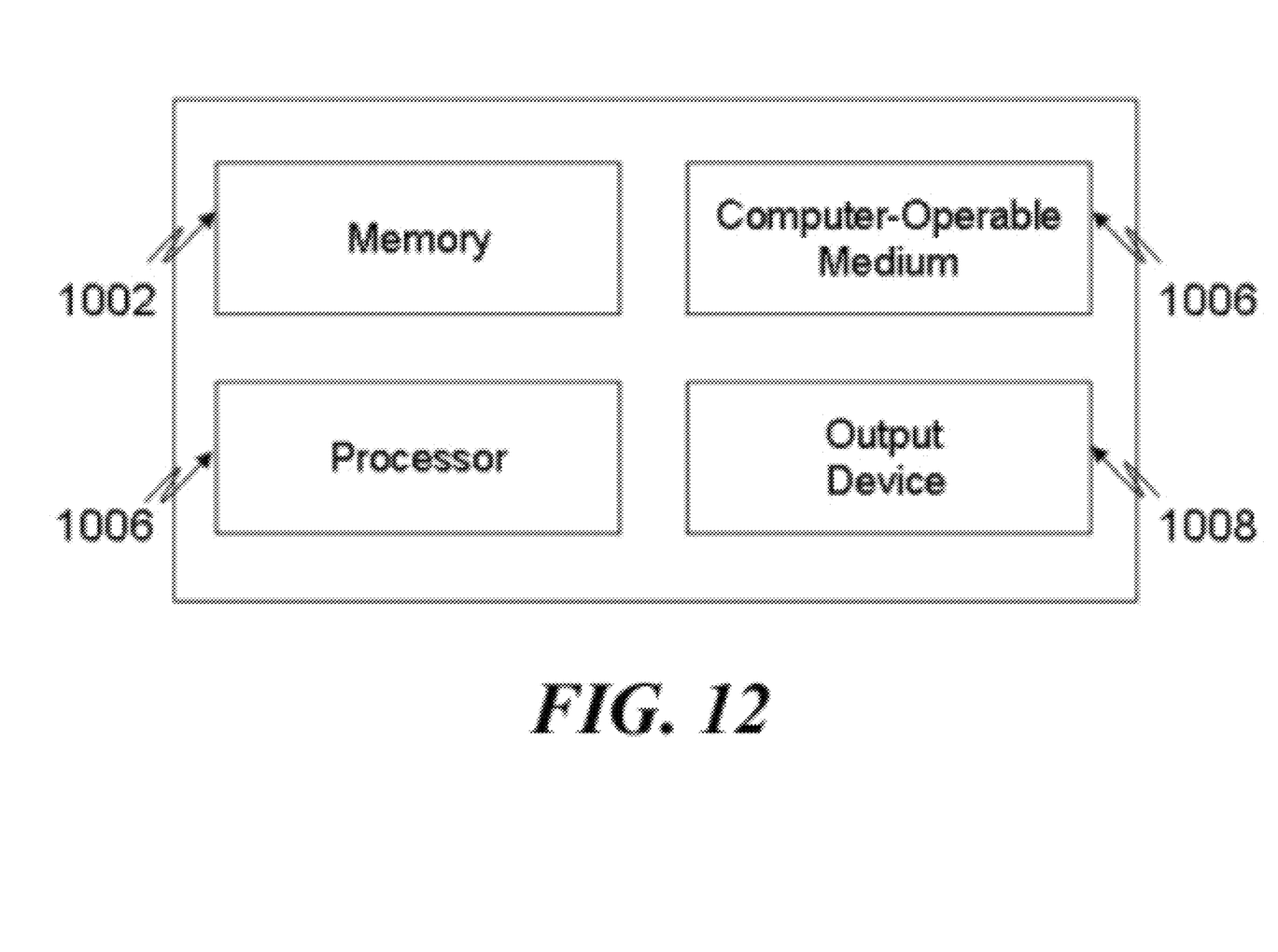
FIG. 12 is a schematic illustration of a system for determining patient specific QT-RR curves and associated confidence limits in accordance with embodiments of the technology.

FIG. 12 is a schematic view illustrating a system 1000 for determining patient-specific QT-RR curves and associated confidence limits in accordance with embodiments of the technology. The system 1000 includes a memory 1002 that at least temporarily contains electrophysiological data for a specific patient. For example, the memory 1002 can contain ECG data recorded during a resting phase and an exercise phase of the protocol. As explained above, the protocol lasts approximately ten minutes and is designed to bring the patient's heart rate to a maximum value. The system 1000 can further include a computer-operable medium containing instructions that: (a) determine the duration of a plurality of QT intervals and associated RR values for a corresponding plurality of heart beats of the specific patient from the electrophysiological data; (b) ascertain a plurality of effective RR intervals for the plurality of heart beats by weight-averaging the RR values according to the equation $\text{EffectiveRR}_i = C \times \text{EffectiveRR}_{i-1} + (1-C)RR_i$, where C is a number between 0 and 1; (c) find a value of $C_f$ defined by a value of C where a curve fitted to the QT intervals and the ascertained effective RR intervals is within a desired standard deviation; and (d) output the value of $C_f$. The system 1000 further includes a processor 1006 and an optional output device 1008. The processor 1006 executes the instructions contained by the computer-operable medium 1004, and the output device 1008 can be a display, printer, electronic media (e.g., memory, network, etc.) or other format that outputs patient-specific QT-RR curves in accordance with the technology.

From the foregoing, it will be appreciated that specific embodiments of the invention have been described herein for purposes of illustration, but well-known processes, structures and functions have not been shown or described in detail to avoid unnecessarily obscuring the description of the embodiments of the invention. Where the context permits, singular or plural terms may also include the plural or singular term, respectively. Unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The term "comprising" is not exclusionary, but rather it is inclusive and used throughout to mean including at least the recited feature(s) such that any number of the same feature and/or additional types of features are not excluded. Similarly, the use of "first" and/or "second" is not exclusionary or otherwise limited to meaning only a first and second feature, but rather the use of "first" and/or "second" is inclusive of more or less of the same or different features.

From the foregoing, it will also be appreciated that specific embodiments of the disclosure have been described herein for purposes of illustration but that various modifications may be made without deviating from the invention. Aspects of the disclosure described in the context of particular embodiments may be combined or eliminated in other embodiments. Further, while advantages associated with certain embodiments of the disclosure may have been described in the context of those embodiments, other embodiments may also exhibit such advantages, but not all embodiments need necessarily exhibit such advantages to fall within the scope of the disclosure. Accordingly, the disclosure can include other embodiments not expressly shown or described above.

I claim:

1. A method, preformed by a computing system, for modeling heart rate adaptation for determining a patient specific QT-RR curve, comprising:
providing electrophysiological data for a specific patient;
determining observed QT durations and observed $RR_i$ values for a plurality of heart beats of the specific patient from the electrophysiological data;
ascertaining, using one or more processers of the computing system, effective RR intervals for the plurality of heart beats by weight-averaging the observed $RR_i$ values according to the equation Effective $RR_i = C \times$ Effective $RR_{i-1} + (1-C) \times [RR_{weighted}]$, where C is a number between 0 and 1, and where $RR_{weighted}$ is based on the observed $RR_i$ value and a predicted $RR_i$ value;
finding a value $C_f$ defined by a value of C where a curve fitted to the observed QT durations and the ascertained effective RR intervals is within a desired standard deviation; and
providing an assessment of a condition of the specific patient based upon the curve defined by the $C_f$.

2. The method of claim 1, wherein $RR_{weighted}$ comprises: $[(RR_i + W \times \text{Predicted } RR_i)/(1+W)]$; and
the Predicted $RR_i$ value is derived from a weighted trend of previous Effective $RR_n$ values with each previous Effective $RR_n$ value weight decreasing as $L^n$, where n is an RR count before a current RR interval and $0 \leq L \leq 1$, and W is a relative averaging Weight between the observed $RR_i$ and Predicted $RR_i$ values, and $W \geq 0$; and finding values $C_f$, $L_f$ and $W_f$ defined by values of C, L and W where a curve $K_f$ fitted to the observed QT durations and the ascertained effective RR intervals is within a desired standard deviation.

3. The method of claim 2, wherein W=0 such that $RR_{weighted}$ equals the observed $RR_i$ value.

4. The method of claim 1, wherein providing electrophysiological data for the specific patient includes providing heart beats obtained during an exercise test and heart beats obtained during a recovery period following the exercise test.

5. The method of claim 2, further comprising:
selecting a series of values for C where $C = C_1, C_2 \ldots, C_n$;
selecting a series of values for L where $L = L_1, L_2 \ldots, L_n$;
selecting a series of values for W where $W = W_1, W_2 \ldots, W_n$;
ascertaining a plurality of sets of effective RR intervals $\{RR_1\}$-$\{RR_n\}$ based on corresponding values of $C_1$ to $C_n$, $L_1$ to $L_n$ and $W_1$ to $W_n$;
fitting a plurality of curves $K_1$ to $K_n$ to the observed QT durations and the corresponding sets of effective RR intervals $\{RR_1\}$-$\{RR_n\}$; and
finding $C_f$, $L_f$ and $W_f$ by selecting the curve $K_f$ corresponding to one of the curves $K_1$ to $K_n$ with the best fit to the observed QT durations and the ascertained effective RR intervals $\{RR_1\}$-$\{RR_n\}$.

6. The method of claim 5, further comprising performing a QT test for a drug by determining a first curve $K_{f1}$ for the specific patient before administering the drug, determining a second curve $K_{f2}$ for the specific patient after administering the drug, and determining a shift in QT between curves $K_{f1}$ and $K_{f2}$ for at least one ascertained effective RR interval.

7. The method of claim 1, further comprising estimating risk of long QT syndrome for the specific patient, wherein estimating risk includes comparing the patient specific QT-RR curve to a plurality of established QT-RR curves from a population of people.

8. The method of claim 7, wherein a higher observed QT duration on the patient specific QT-RR curve when compared to the plurality of established QT-RR curves from a population of people indicates a higher risk of long QT syndrome.

9. The method of claim 5, further comprising estimating risk of long QT syndrome for the specific patient, wherein estimating risk includes comparing a slope of observed QT durations at ascertained effective RR intervals for the curve $K_f$ for the specific patient to a plurality of established slopes of observed QT durations at corresponding effective RR intervals for a population of people.

10. The method of claim 1, wherein the curve fitted to the observed QT durations and the ascertained effective RR intervals is a polynomial.

11. The method of claim 1, wherein providing electrophysiological data for the specific patient includes providing heart beats obtained during a pre-exercise test rest segment, during an exercise test, and during a recovery period after the exercise test.

12. The method of claim 1, wherein providing electrophysiological data for the specific patient includes providing heart beats obtained continuously during normal daily activities.

13. The method of claim 1 further comprising administering the specific patient a therapeutic agent prior to providing electrophysiological data.

14. The method of claim 13 further comprising estimating risk of therapeutic agent-induced long QT for the specific patient, wherein estimating risk includes comparing the patient specific QT-RR curve to a plurality of established QT-RR curves from a population of people.

15. A method, performed by a computing system, for modeling heart rate adaptation for determining a patient specific QT-RR curve, comprising:
  providing electrophysiological data for a specific patient during an exercise test and during a recovery period following the exercise test;
  determining first observed QT durations and first observed $RR_i$, values for a plurality of exercise test heart beats;
  determining second observed QT durations and second observed $RR_i$, values for a plurality of recovery period heart beats;
  ascertaining, using one or more processors of the computing system, first effective RR intervals for the plurality of exercise test heart beats by weight-averaging the first observed $RR_i$, values according to the equation Effective $RR_i = C \times$ Effective $RR_{i-1} + (1-C) \times [RR_{weighted}]$, where C is a number between 0 and 1, and where $RR_{weighted}$ is based on the first observed $RR_i$ value and a first predicted $RR_i$ value;

ascertaining, using one or more processors of the computing system, second effective RR intervals for the plurality of recovery period heart beats by weight-averaging the second observed $RR_i$ values according to the equation Effective $RR_i = C \times$ Effective $RR_{i-1} + (1-C) \times [RR_{weighted}]$, where C is a number between 0 and 1, and where $RR_{weighted}$ is based on the second observed $RR_i$ value and a second predicted $RR_i$ value;

finding a value $C_f$ defined by a value of C where a curve fitted to the first and second observed QT durations and the first and second ascertained effective RR intervals is within a desired standard deviation; and providing an assessment of a condition of the specific patient based upon the curve defined by the value $C_f$.

* * * * *